United States Patent [19]

Nepom

[11] Patent Number: 4,971,902

[45] Date of Patent: Nov. 20, 1990

[54] DIAGNOSTIC PROBE FOR RHEUMATOID ARTHRITIS PREDISPOSITION

[75] Inventor: Gerald T. Nepom, Bainbridge Island, Wash.

[73] Assignee: Virginia Mason Research Center, Seattle, Wash.

[21] Appl. No.: 115,253

[22] Filed: Oct. 30, 1987

[51] Int. Cl.$^5$ .......................... C01N 33/00; C12Q 1/68; C07H 19/06; C07H 15/12

[52] U.S. Cl. .......................................... 435/6; 536/26; 536/27; 935/78; 436/94; 435/810

[58] Field of Search ....................... 435/6, 810; 536/26, 536/27; 935/78; 436/94

[56] References Cited

U.S. PATENT DOCUMENTS 4,707,440 11/1987 Stavrianopoulos ..................... 435/6

OTHER PUBLICATIONS

Gregersen, et al., PNAS, vol. 83, pp. 2642–2646, 1986.
Connors, et al., PNAS, vol. 80, pp. 278–282, 1983.
Kim, et al., PNAS 82, pp. 8139–8143, 1985.
Caruthers, In: S. M. Weisman (ed): Methods of DNA & RNA Sequencing, pp. 1–22, Praeger Publishers, N.Y., N.Y. 1983.
Nepom, et al., (I) in the Immunology of Diabetes Mellitus, M. Jaworski, et al. eds., Elsevier Science Publishers, pp. 9–20, 1986.
Nepom, et al., (II) J. Clin. Invest. 74: 287–291, 1984.
Stasney N. Engl. J. Med. 298: 869–871, 1978.
Festenstein, et al., Nature, vol. 322, pp. 64–67, 1986.
Wordsworth, B., et al., HLA-DR4 Subtype Frequencies in Rheumatoid Arthritis Indicate that DRB1 is the Major Susceptibility Locus within the HLA Class II Region, *Proc. Natl. Acad. Sci.* U.S.A. 86:10049–10053, Dec. 1989.
McMichael, A. J., et al., Increased Frequency of HLA-Cw3 and HLA-Dw4 in Rheumatoid Arthritis, *Arthritis & Rheumatism* 20(5):1037–1042, 1977.
Tiwari, J. L., and Terasaki, P. I., HLA and Disease Associations, New York: Springer-Verlag, pp. 55–64, 1985.
Jeraquemada, D., et al., HLA and Rheumatoid Arthritis: A Combined Analysis of 440 British Patients, *Annals of the Rheumatic Diseases* 45:627–636, 1986.
Goronzy, J., et al., Shared T Cell Recognition Sites on Human Histocompatibility Leukocyte Antigen Class II Molecules of Patients with Seropositive Rheumatoid Arthritis, J. Clin. Invest. 77:1042–1049, Mar. 1986.
Gregersen, P. K., et al., An Approach to Understanding the Molecular Genetics of Susceptibility to Rheumatoid Arthritis, Arthritis and Rheumatism 30(11):1205–1213, Nov. 1987.
Nepom, B. S., et al., Specific HLA-DR4-Associated Histocompatibility Molecules Characterize Patients (List continued on next page.)

*Primary Examiner*—Christine Nucker
*Assistant Examiner*—Karen I. Krupen
*Attorney, Agent, or Firm*—Christensen, O'Connor, Johnson & Kindness

[57] ABSTRACT

Oligonucleotide probes for diagnosing predisposition to rheumatoid arthritis, capable of specifically hybridizing with $$5'\text{-TACGGGGTTGR}_1\text{GAGAGCTT-}3'$$

or $$3'\text{-AR}_2\text{GCCCCAACR}_3\text{CR}_2\text{CR}_2\text{CGAA-}5'$$

wherein A is adenine, C is cytosine, G is guanine, T is thymine, $R_1$ is GT or TG, $R_2$ is T or uracil, and $R_3$ is CA or AC. Or, capable of specifically hybridizing with $$5'\text{-GGAGCAGAR}_2\text{GCGGGCCGCGG-}3'$$

or $$3'\text{-CCR}_2\text{CGR}_2\text{CR}_2\text{R}_3\text{CGCCCGGCGCC-}5'$$

wherein $R_1$ is A or G, $R_2$ is T or uracil, and $R_3$ is $R_2$ or C.

22 Claims, 4 Drawing Sheets

OTHER PUBLICATIONS with Seropositive Juvenile Rheumatoid Arthritis, J. Clin. Invest. 74:287-291, 1984.

Holbeck, S. L., and G. T. Nepom, Exon-Specific Oligonucleotide Probes Localize HLA-DQ$_\beta$ Allelic Polymorphisms, Immunogenetics 24:251-258, 1986.

Nepom, G. T., et al., Specific HLA Class II Variants Associated with IDDM, in the Immunology of Diabetes Mellitus, M. Jaworski, et al., eds., Elsevier Science Publishers, pp. 9-20, 1986.

Nepom, G. T., et al., Identification of HLA-Dw14 Genes in DR4+ Rheumatoid Arthritis, the Lancet ii:1002-1005, Nov. 1986.

Nepom, G. T., et al., The Molecular Basis for HLA Class II Associations with Rheumatoid Arthritis, J. Clin. Immunol. 7(1):1-7, 1987.

Festenstein, H., et al., New HLA DNA Polymorphisms Associated with Autoimmune Diseases, *Nature* 322:64-67, Jul. 1986.

The Merck Manual of Diagnosis and Therapy, 15th ed., pp. 1229-1246, 1793-1798, and 2095-2096, Merck Sharp & Dohme Research Laboratories, Rahway, N.J., 1987.

Nepom, G. T., et al., HLA Genes Associated with Rheumatoid Arthritis: Identification of Susceptibility Alleles using Specific Oligonucleotide Probes, *Arthritis and Rheumatism* 32(1):15-21, Jan. 1989.

Nelson, J. L., et al., T Cell Clone Analysis of HLA-D Epitopes in Patients with Rheumatoid Arthritis, Abstract from the American Rheumatism Association 53rd Annual Scientific Meeting, Jun. 12-17, 1989.

HLA CLASS II GENES ON CHROMOSOME 6

DPβ2 DPα2 DPβ1 DPα1 / DZα DOβ / DQβ2 DQα2 DQβ1 DQα1 / DRβ1 DRβ2 DRβ3 DRα

HLA SEROLOGICAL SPECIFICITIES OF CELL-LINES USED FOR GENOMIC ANALYSIS

| Cell-line | Diagnosis | Age at onset | HLA-A | HLA-B | HLA-C | HLA-DR | HLA-DQ | TA10* |
|---|---|---|---|---|---|---|---|---|
| 811 | RA | 49 | 2,24 | 7,40 | 3,7 | 4 | 3 | − |
| 812 | RA | 37 | 25,32 | 44 | 5,6 | 4 | 3 | + |
| 815 | RA | 22 | 2 | 44,39 | 5,7 | 4 | 3 | + |
| 820 | RA | 79 | 2,24 | 21,62 | 3,7 | 4 | 3 | − |
| 795 | RA | 58 | 2,31 | 44,27 | 1,5 | 4 | 3 | + |
| 805 | RA | 17 | 2,28 | 35,38 | 4 | 4 | 3 | + |
| 883 | RA | 34 | 2,3 | 8,44 | 5,7 | 4 | 3 | + |
| 777 | RA | 58 | 2 | 5 | 1 | 4,5 | 3 | + |
| 788 | RA | 38 | 3,24 | 18,62 | 3,7 | 4,5 | 3 | + |
| ER | Dw4 HTC† | : | 2 | 44 | 5 | 4 | 3 | + |
| BIN40 | Dw14 HTC | : | 2,31 | 14,60 | − | 4 | 3 | − |
| 256 | JRA Dw4/w14 | : | 1,2 | 8,15 | − | 4 | 3 | + |

*TA10 is defined by monoclonal antibody 9w790, and characterises an allelic variant of DQw3 called DQβ3·1[18]. †Homozygous typing cell.

Fig. 5.

DIAGNOSTIC PROBE FOR RHEUMATOID ARTHRITIS PREDISPOSITION

TECHNICAL FIELD

This invention relates generally to genetic engineering and more particularly to DNA and RNA probes useful for diagnosing predisposition to disease states, specifically rheumatoid arthritis.

BACKGROUND OF THE INVENTION

Genetic screening for inherited diseases based on the use of specific gene probes is a promising technology that will augment both the breadth and the precision of genetic diagnostic testing. There are an estimated 3,000 genetic disorders known which result from a single gene mutation, for which the application of specific gene probes is of direct value. In addition, however, there are a number of common disorders, such as rheumatoid arthritis (RA) and type I diabetes, which result not from a single gene mutation but from a combination of genetic and possibly environmental factors. In such cases, genetic inheritance determines the predisposition, or disease risk, associated with a large proportion of clinical disease. Thus, genetic testing for rheumatoid arthritis should be viewed as the identification of genetic predisposition, distinct from the more conventional notion of a single gene defect resulting in a specific inherited disease.

The identification of a particular gene associated with predisposition to rheumatoid arthritis can be viewed from two different perspectives. On the one hand, the gene being detected may be linked on the chromosome to other genes which actually confer disease susceptibility, in which case the gene being tested would function as a marker gene. On the other hand, the gene being identified may itself contribute directly to disease, but only if other genetic elements or appropriate environmental agents are present. Both of these concepts are important for understanding the genetic predisposition to rheumatoid arthritis.

The major genetic contribution to both rheumatoid arthritis and type I diabetes is encoded in a portion of chromosome 6 known as the major histocompatibility complex (MHC). Within this gene complex, a series of 14 linked genes constitutes the human leukocyte antigen (HLA) class II gene cluster. Products of these class II genes are essential in the normal immune response for the triggering of the activation steps which lead to immunity. Even when the immune system is activated inappropriately, and attacks normal tissue, causing autoimmunity, these class II molecules play an essential role in the immune activation which leads to disease. This has led to the concept that the role of the HLA class II genes in autoimmune diseases such as rheumatoid arthritis is to function as a permissive molecular signal, like a "green light" which signals the immune system to proceed with an attack on a particular target. In the case of rheumatoid arthritis the target is assumed to be some tissue related to synovial lining of the joints. Thus, in many respects, the question of genetic predisposition in rheumatoid arthritis is an issue of identifying which HLA class II genes are responsible for aberrant signals in the activation of the autoimmune response.

The association of HLA class II genes with rheumatoid arthritis and with type I diabetes has been suspected for some time. The products of HLA genes carry the HLA typing specificities, which are conventionally measured using serologic reactivities. These typing specificities are a partial measure of genetic polymorphisms within the HLA gene complex. One of these serologic polymorphisms, known as HLA DR4, is present in approximately 70-75% of patients with either classic rheumatoid arthritis or type I diabetes. The utility of this serologic marker for disease predisposition analysis is limited, however, by the fact that approximately 35% of the normal population also type as HLA DR4.

SUMMARY OF THE INVENTION

In the research described below, specific gene probes were developed that distinguish not only among different class II genes in DR4 positive haplotypes, but also between several polymorphic alleles for several of these linked loci. Using these probes, the following discoveries were made: Different patterns of linked genes are present on different individuals who all type as HLA DR4. Different linked genes account for the susceptibility of DR4 individuals to rheumatoid arthritis compared to type I diabetes, even though they both "type" as HLA DR4. Notably, two specific variants, the Dw4 and Dw14 alleles, of one of these genes are highly associated with susceptibility to rheumatoid arthritis; the presence of both alleles in a single individual confers greater than 100-fold increased relative risk. Thus, specific gene probes based on individual gene sequences can be used for oligonucleotide typing to identify individuals having the polymorphic variants associated with genetic susceptibility to rheumatoid arthritis.

The invention provides such oligonucleotide probes, useful for diagnosing predisposition or susceptibility to rheumatoid arthritis, in the form of an oligonucleotide capable, in one embodiment, of specifically hybridizing with the nucleotide sequence $$5'\text{-TACGGGGTTGR}_1\text{GAGAGCTT-3}'$$

or $$3'\text{-AR}_2\text{GCCCCAACR}_3\text{CR}_2\text{CR}_2\text{CGAA-5}'$$

wherein A is adenine, C is cytosine, G is guanine, T is thymine, $R_1$ is GT or TG, $R_2$ is T or uracil, and $R_3$ is CA or AC. In another embodiment, the probe is capable of specifically hybridizing with the nucleotide sequence $$5'\text{-GGAGCAGAR}_1\text{GCGGGCCGCGG-}'3$$

or $$3'\text{-CCR}_2\text{CGR}_2\text{CR}_2\text{R}_3\text{CGCCCGGCGCC-5}'$$

wherein A is adenine, C is cytosine, G is guanine, T is thymine, $R_1$ is A or G, $R_2$ is T or uracil, and $R_3$ is $R_2$ or C.

The subject probes are useful for diagnosing predisposition to rheumatoid arthritis by assaying for the presence of the Dw14 DR$\beta$ allele, alone or in combination with the Dw4 DR$\beta$ allele, in patient-specific polynucleotides (isolated DNA and/or RNA, or restriction fragments thereof) or cells. The Dw4 probe preferably includes at least 15 sequential nucleotides selected from the sequence $$3'\text{-TGCCCCAACCACTCTCGA-5}'$$

or

5'-ACGGGGRRGGRGAGAGCR-3' or

3'-CTCGTCTTGCCCGGCGC-5' or

5'-GAGCAGAAGCGGGCCGCG-3' wherein R is thymine or uracil. The subject Dw14 probe preferably includes at least 15 sequential nucleotides selected from the sequence

3'-TGCCCCAACACCTCTCGA-5' or

5'-ACGGGGRRGRGGAGAGCR-3' or

3'-CTCGTCTCCGCCCGGCGC-5' or

5'-GAGCAGAGGCGGGCCGCG-3' wherein R is thymine or uracil.

The probes may be labeled with a detectable marker, such as an enzyme or biotin, and will typically be supplied in a diagnostic kit in combination with a substratum capable of binding polynucleotides or cells, a restriction enzyme, and/or a detergent.

DETAILED DESCRIPTION OF THE PREFERRED EMBODIMENT

Figures 1, 2:
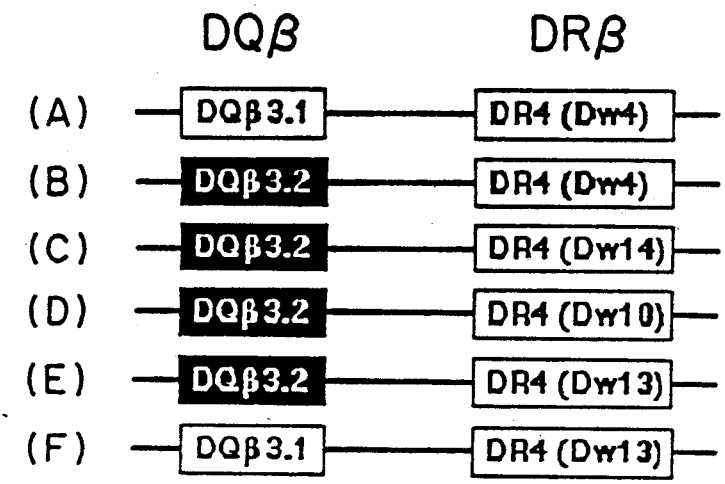
FIG. 1 depicts gene organization of the class II region of the HLA complex on human chromosome 6.
FIG. 2 diagrams the DR and DQ specificities associated with HLA-DR4, organized by haplotypes.

FIG. 1 illustrates the genes on chromosome 6 which constitute the HLA class II genetic complex. Several of these genes are highly polymorphic; that is, they exist in numerous allelic forms in the normal population. For instance, at least 50 alleles of the DRβ1 locus, and a dozen or so alleles of the DQα and DQβ loci are known to exist. In the FIGURE, asterisks mark genes known to be expressed: the DR and Dw allelic series, including Dw4(DR) and Dw14(DR) genes, representing alleles of the DRβ1 locus. The DQβ3.1(DQw3) and DQβ3.2(DQw3) genes represent alleles of the DQβ1 locus. Protein products of the genes marked with an asterisk have been identified on the surface of lymphoid cells where they participate in the activation events triggering the immune response. Thus, these genes encode the structural proteins used in the signaling events critical for the immune system activation in health and disease. The HLA DR4 specificity is carried by products of the DRβ1 locus. At least five different DRβ1 alleles all carry the HLA DR4 serologic specificity, and other alleles do not, but instead carry HLA specificities known as DR1, DR2, etc.

As shown in FIG. 2, each of the five alleles of DRβ1 genes on DR4 positive haplotypes have been given different names, such as Dw4, Dw14, Dw10, Dw13, Dw15. Each of these different DRβ1 alleles is linked to a polymorphic DQβ allele. As noted in the FIGURE, the DQβ alleles are designated DQ3.1, DQ3.2, or DQx. An individual who "types" using conventional methodology as HLA DR4 potentially will carry any of the haplotypes illustrated in FIG. 2. In other words, up to five different alleles of DRβ and three different alleles of DQβ may be represented with the linkage patterns shown. In order to analyze the specific individual genes which account for the HLA DR4 association with rheumatoid arthritis, it was necessary to design techniques to distinguish among all these different DR and DQ alleles.

All of the different DR4 positive DRβ1 alleles are very closely related. They differ from each other by as few as one amino acid or as many as five amino acids. In keeping with this limited divergence, restriction enzyme recognition sites are conserved among these different alleles. In other words, restriction fragment linked polymorphisms (RFLP) do not distinguish among the different DR4 positive DRβ1 alleles. Therefore, it was necessary to design allele-specific oligonucleotide probes with very stringent hybridization conditions to distinguish between these closely related genes.

Referring to FIG. 2, three different alleles of the DQβ gene are found on DR4 positive haplotypes. These three alleles are fairly divergent from each other, and can be distinguished by either restriction enzyme polymorphisms (RFLP) or specific oligonucleotide probes.

Figure 3:
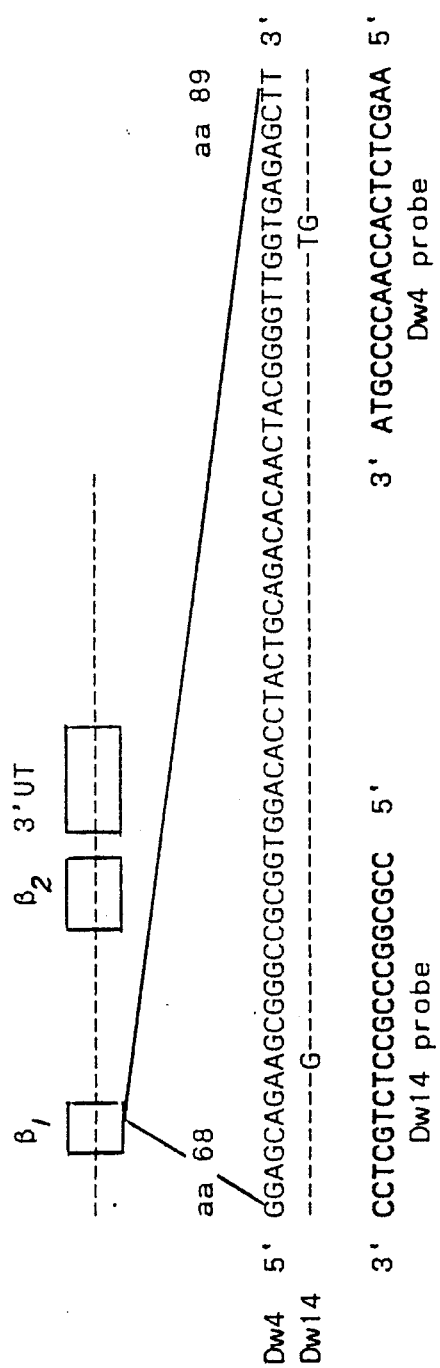
FIG. 3 illustrates the construction of representative allele-specific oligonucleotide DNA probes to distinguish between the Dw4 and Dw14 DRβ genes.

FIG. 3 illustrates the construction of allele-specific oligonucleotide DNA probes designed to distinguish between the Dw4 and Dw14 DRβ1 genes. As shown in the FIGURE, within the nucleotide sequence for the DR4β gene corresponding to amino acids 68–89 in the HLA beta chain, three nucleotide differences exist between the Dw4 and Dw14 genes. An exemplary Dw4 DNA probe corresponds to a twenty nucleotide sequence that is mismatched by two nucleotides from Dw14 as indicated. The prototype Dw14 DNA probe corresponds to a twenty nucleotide region that differs by one nucleotide from the Dw4 sequence. Under stringency conditions such that a hybridization signal is detected only when a probe is 100% analogous with the sample, the presence or absence of the Dw4 or Dw14 sequence can be confirmed using these probes. By first digesting genomic DNA with EcoR I, discrimination is assured between the assayed sequence (Dw4 or Dw14) and other potential DR-related genes on DR4 haplotypes and on a patient's other haplotype which could potentially cross-hybridize. In all such cases, the Dw4 or Dw14 genes, if present, appear on an 11 kilobase (kb) EcoR I fragment.

Figure 4A:
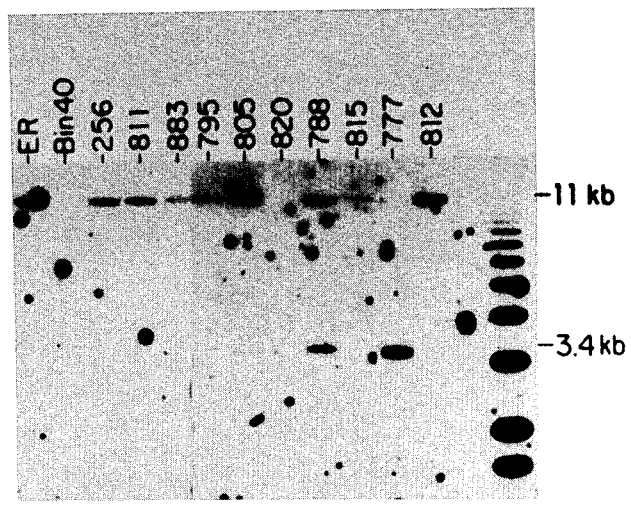
FIGS. 4A and 4B depict representative hybridization analyses of Dw4 and Dw14 gene sequences with the subject probes; and, FIG. 5 depicts the HLA serological specificities of the cell lines used for genomic analysis in the Example.
Figure 4B:
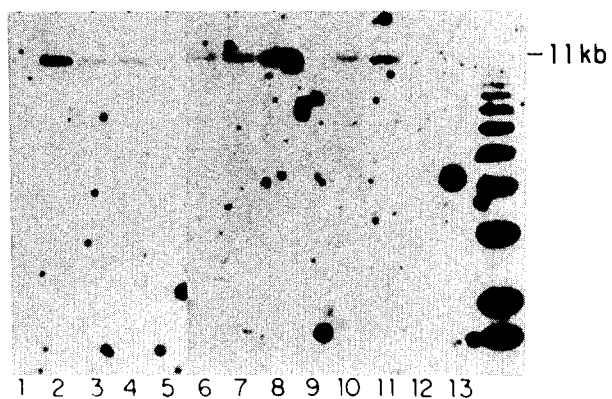

FIG. 4 illustrates the use of these probes in a study of classic adult rheumatoid arthritis. In lanes 1 to 3 in panel A, the Dw4 oligonucleotide probe gave a hybridization signal with control Dw4 cell line ER but not with Dw14 cell line BIN40; eight of the ten patients illustrated in lines 3 to 12 gave a positive Dw4 signal on their EcoR I-digested genomic DNA at 11 kb. In panel B, the Dw14 oligonucleotide probe was used on the same DNA samples. Here, the controls in lanes 1 to 3 are reversed, with no signal on cell line ER, and a positive signal on cell line BIN40, verifying the ability of the probe to detect a single nucleotide change. Again, eight of ten patients illustrated are positive for the Dw14 gene. While one patient tested as only Dw4, and one tested as only Dw14, the remainder tested as heterozygous, carrying both Dw4 and Dw14. These data are reported in more detail in Nepom, G. T., et al., The Lancet ii: 1002-1005, 1986, the disclosure of which is hereby incorporated by reference.

Both the Dw4 gene and Dw14 gene confer increased susceptibility (or predisposition) to rheumatoid arthritis. Other DR4-positive DRβ1 alleles have not been found to be associated; nor are the various DQ alleles associated with rheumatoid arthritis. A statistical summary of these associations, derived from a study of seropositive juvenile rheumatoid arthritis, indicated that the presence of both Dw4 and Dw14 genes is associated with a greater than 100-fold relative risk.

In spite of the high association of the Dw4 and Dw14 alleles, individually and in combination, with rheumatoid arthritis, it is important to emphasize that these genes, as with other HLA genes associated with autoimmune disease, predispose the carrier toward, but are not solely responsible for the inherited disease. In that sense, these data confirm what has been observed in studies of identical twins: that diseases such as rheumatoid arthritis are not simple single-gene disorders. Multiple factors, possibly including more than one gene, and probably including some environmental interactions, presumably act in concert to lead to the full-blown disease syndrome. In this context, the particular predisposition gene or genes play some key permissive role, but are not per se sufficient for disease expression. Nevertheless, identification of individuals having the Dw4 and/or Dw14 alleles is of direct diagnostic value for assessing predisposition to rheumatoid arthritis.

The invention thus provides probes useful for diagnosing predisposition to rheumatoid arthritis, in the form of oligonucleotides capable of identifying and specifically binding to the Dw4 and/or Dw14 DRβ genes. For the Dw4 allele, a representative probe specifically hybridizes with one of the following distinguishing gene sequences:

$$5'\text{-TACGGGGTTGGTGAGAGCTT-}3' \tag{1}$$

or $$3'\text{-ATGCCCCAACCACTCTCGAA-}5' \tag{2}$$

or $$5'\text{-GGAGCAGAAGCGGGCCGCGG-}3' \tag{3}$$

or $$3'\text{-CCTCGTCTTCGCCCGGCGCC-}5'. \tag{4}$$

Since the Dw4 allele is expressed, e.g., in monocytes and B cells, RNA probes are also provided that are capable of specifically hybridizing with the RNA sequences:

$$3'\text{-AUGCCCCAACCACUCUCGAA-}5' \tag{5}$$

or $$3'\text{-CCUCGUCUUCGCCCGGCGCC-}5'. \tag{6}$$

The Dw14 probe may include an oligonucleotide capable of specifically hybridizing with one of the following nucleotide sequences, wherein R is thymine or uracil (U):

$$5'\text{-GGAGCAGAGGCGGGCCGCGG-}3' \tag{7}$$

or $$3'\text{-CCRCGRCRCCGCCCGGCGCC-}5' \tag{8}$$

or $$5'\text{-TACGGGGTTGTGGAGAGCTT-}3' \tag{9}$$

or $$3'\text{-ARGCCCCAACACCRCRCGAA-}5'. \tag{10}$$

By "specifically hybridizing" as used herein is meant that the subject probes are capable of hybridizing either with the sense or antisense strand of the Dw4 or Dw14 alleles, or with RNA transcribed therefrom, at a stringency condition where a single base mismatch does not hybridize. Those skilled in the art will recognize that the stringency conditions for various hybridization assay formats will depend on the constellation of temperature, ionic concentration, and pH. Generally, for optimum DNA:DNA or RNA:RNA hybridization, the temperature is inversely related to salt concentration; and the pH should be held, e.g., for 15 nucleotide sequences ("15-mers"), in the range of from about 6.8 to about 7.4. For RNA:DNA hybridizations, similar assay conditions apply, but lower temperatures (accompanied by higher salt concentrations) are generally employed than for the DNA:DNA hybridizations.

In other words, the subject probes should exactly complement all or part of any of the oligonucleotide sequences (1) through (10). Preferably, the bases complementary to terminal sequences of (1) through (6) are not included in the probe construction, in order to increase the hybridization efficiency. Accordingly, the subject probes for identifying the Dw4 allele will generally contain sequential nucleotides selected from the following sequences (wherein R is T or U):

$$3'\text{-TGCCCCAACCACTCTCGA-}5' \tag{11}$$

or $$5'\text{-ACGGGGRRGGRGAGAGCR-}3' \tag{12}$$

or $$3'\text{-CTCGTCTTCGCCCGGCGC-}5' \tag{13}$$

or $$5'\text{-GAGCAGAAGCGGGCCGCG-}3'. \tag{14}$$

The subject probes for identifying the Dw14 allele will generally contain sequential nucleotides selected from the following sequences:

$$3'\text{-TGCCCCAACACCTCTCGA-}5' \tag{15}$$

or

5'-ACGGGGRRGRGGAGAGCR-3'    (16)

or

3'-CTCGTCTCCGCCCGGCGC-5'    (17)

or

5'-GAGCAGAGGCGGGCCGCG-3'.    (18)

The requisite specificity, with respect to the human genome, can be achieved by constructing the Dw4 probe with any 15-nucleotide sequence from within (11), (12), (13), or (14); and the Dw14 probe with any 15-mer from within (15), (16), (17), or (18). Preferably, the probe should be such a 16-mer, which is considered to be optimal for commercial diagnostic applications at room temperature. For higher signal specificity, longer oligonucleotide sequences, including the 21-base sequences complementing (1) through (10), can be selected, especially for clinical laboratory applications where auxiliary equipment for achieving higher hybridization temperatures is available.

For maximum efficiency, the subject probes contain nucleotide sequences from the central regions of (11) through (18). Thus, in the most preferred embodiment, the Dw4 probes will contain or include the following sequences:

3'-CCCAACCACTCTCG-5'    (19)

or

5'-GGGRRGGRGAGAGC-3'    (20)

or

3'-CTCGTCTTCGCCCGG-5'    (21)

or

5'-GAGCAGAAGCGGGCC-3'.    (22)

The most preferred embodiments of the Dw14 probes will contain or include any of the following sequences:

3'-CCCAACACCTCTCG-5'    (23)

or

5'-GGGRRGRGGAGAGC-3'    (24)

or

3'-CTCGTCTCCGCCCGG-5'    (25)

or

5'-GAGCAGAGGCGGGCC-3'.    (26)

Such oligonucleotides can be readily synthesized by known techniques and available reagents and equipment. The subject probes can be detected or made detectable under various assay conditions in a number of conventional ways. For example, a radioisotope can be incorporated into the probe during oligonucleotide synthesis. Alternatively, an enzyme such as alkaline phosphatase can be conjugated to the probe prior to the assay, or a biotinylated probe can be employed in the assay and hybrids subsequently detected with an avidinized enzyme, e.g., streptavidin-alkaline phosphatase. Luciferins are also suitable for marking the oligonucleotides to make a probe, and the list of presently available detectable markers also includes fluorophores and other luminophores, enzyme inhibitors as well as coenzymes, paramagnetic metals and other spin labels.

The subject DNA and RNA probes can be employed in a wide variety of existing diagnostic hybridization assays, which generally include the steps of contacting patient-specific nucleic acids, either DNA or RNA or both, with an oligonucleotide probe capable of specifically hybridizing with a disease-associated polynucleotide sequence, and thereafter determining the presence or absence of the disease-associated DNA or RNA in the patient-specific sample by detecting DNA:DNA, RNA:RNA, DNA:RNA, or RNA:DNA hybrids formed between the probe and the patient-specific polynucleotides. In such assays, hybridization can occur either on isolated nucleic acids or in situ, e.g., within patient-specific leukocytes, using available protocols in which the nuclear and/or plasma membranes of patient cells are permeabilized with detergents such as octoxynols (particularly Triton X-100) prior to incubation with the probe.

Also provided are diagnostic kits useful for diagnosing predisposition to rheumatoid arthritis, the kits including an oligonucleotide probe capable of specifically hybridizing with the Dw14 DR$\beta$ allele, alone in combination with a second oligonucleotide probe capable of specifically hybridizing with the Dw4 DR$\beta$ allele. Since rheumatoid arthritis is associated with the presence of either allele, both the Dw4 and Dw14 probes will typically be simultaneously assayed. Where resolution of Dw4/Dw14 heterozygosity is desired, the two probes may be labeled with different markers, such as fluorophores having different emission spectra.

The subject probes will typically be supplied in diagnostic test kits in combination with one or more of the following reagents. A substratum capable of adsorbing or otherwise binding DNA and/or RNA will often be supplied with the probes. Available substrata for this purpose include membranes of nitrocellulose, nylon, or derivatized nylon that are generally characterized by bearing an array of positively charged substituents. One or more restriction enzymes, particularly EcoR I, may be furnished in the kit, as may nonhuman polynucleotides such as calf thymus DNA or salmon sperm DNA. For in situ hybridization, a detergent such as Triton X-100 may alternatively be supplied, along with a substratum, such as a transparent microscope slide, for binding the patient's cells throughout the permeabilization, probe incubation and hybridization, and detection steps of the assay.

The invention is further illustrated by the following specific Example.

EXAMPLE

Men and women who attended the Virginia Mason Clinic Rheumatology Section during 1985 were typed for HLA antigens. All patients had classic rheumatoid arthritis according to American Rheumatism Association criteria. Only Caucasian patients with positive rheumatoid factor and symmetrical polyarthritis were included; most patients had joint erosions and rheumatoid nodules shown by radiography. Of 45 patients who met these criteria, seven were phenotypically homozygous for HLA DR4. As discussed below, two additional heterozygous DR4/5 patients were included in this study. Control frequencies for HLA specificities were measured in 243 random blood donors. Control subjects were also Caucasians drawn from similar ethnic populations.

DNA was prepared from B-lymphoblastoid lines, transformed by Epstein Barr virus, of patients' peripheral blood lymphocytes. The serological specificities of the cell lines are shown in FIG. 5.

Cell lysates were digested with proteinase K followed by extraction with phenol:chloroform:isoamyl alcohol (25:24:1) and ethanol precipitation. Purified DNA was digested with restriction endonuclease EcoR I (Bethesda Research Laboratories, BRL) for 16 hours and electrophoresed on a 1% agarose gel in TAE buffer (40 mmol/l "Tris"-acetate, 1 mmol/l edetic acid) for 16 hours at 1.5 V/cm. Markers on each gel consisted of a 1 kb ladder (BRL) end-labeled with $\alpha$-P-d-adenosine triphosphate (ATP) with the use of T4 polynucleotide kinase. After electrophoresis, the gels were denatured, neutralized, and dried on Whatman 3MM paper. They were soaked briefly in water to remove the backing paper, prehybridized for 1 hour at 53° C. (for Dw4 hybridizations) or 55° C. (for Dw14 hybridizations) in $6 \times$ NET (0.6 mol/l NaCl; 0.18 mol/l "Tris" HCl, pH 8.0; 6 mmol/l edetic acid) containing 250 $\mu$g/ml tRNA (Sigma Chemical Co.) and were then hybridized for 3 hours at 53° C. (Dw4) or 55° C. (Dw14) in $6 \times$ NET, 10% dextran sulphate, $5 \times$ Denhardts' solution, 5 mmol/l edetic acid, 0.1% sodium dodecyl sulphate (SDS), 0.05% "Noniodet P-40," 250 $\mu$g/ml tRNA, and $10^7$ cpm/ml of the appropriate oligonucleotide end-labeled with $\alpha$-$^{32}$P-dATP and T-4 polynucleotide kinase to give a specific activity of $10^9$ cpm/$\mu$g. Gels were washed with $5 \times$ salt and sodium citrate and 0.5% SDS twice at room temperature for 10 min, and twice at 55° C. for 30 min followed by washing with 3.2 mol/l tetramethylammonium chloride containing 0.5% SDS once at 55° C. for 10 min and once at 58° C. for 30 min. The gels were wrapped in plastic and exposed to Kodak XAR film for 2 to 4 days at $-70$° C. with Cronex "Lightening Plus" intensifying screens.

The construction of exemplary allele-specific oligonucleotide DNA probes designed to distinguish between the Dw4 and Dw14 DR$\beta$ genes is shown schematically in FIG. 3. The probes had the following sequences: 3'-CCTCGTCTCCGCCCGGCGCC-5' (Dw14 probe) and 3'-ATGCCCCAACCACTCT-CGAA-5' (Dw4 probe). Probes Dw4 and Dw14 can be readily synthesized, e.g., using an Applied Biosystems automated DNA synthesizer, by phosphoramidite analog chemistry as described by M. H. Carruthers in Methods of DNA and RNA Sequencing, pp 1–22, Weismann, S. M., ed., Praeger Publishers, N.Y., 1983, hereby incorporated by reference.

Some other DR genes, including HLA DR5, contain a sequence homologous to the Dw4 DNA probe; see Tieber, V. L., et al., J. Biol. Chem. 261:2738–2742, 1968. However, after digestion of genomic DNA with the restriction enzyme EcoR I, the DR5 gene occurs on a fragment of 3.4 kb, which is easily distinguishable from the 11 kb fragment that is detected with the DR4 probes. EcoR I-digested genomic DNA also discriminates between other potentially DR-related genes on DR4 haplotypes, such as the DRw53 genes and DR4-related pseudogenes (Kim, S. J., et al., Proc. Natl. Acad. Sci. U.S.A. 82:8139–8143, 1985). These cross-hybridizing sequences, if present, would likewise be on EcoR I fragments easily distinguishable from the 11 kb DR4-associated band.

Referring to FIG. 4, the first three lanes of panel A show the hybridization patterns with the Dw4 oligonucleotide probe obtained from genomic DNA of cell line ER, homozygous for Dw4; cell-line BIN40, homozygous for Dw14; and cell-line 256, heterozygous for Dw4 and Dw14. Each of these cell lines has been extensively characterized by means of HLA-D analysis, electrophoresis of HLA DR proteins, and restriction-enzyme analysis of DR$\beta$ genes. The Dw4 probe gave a strong hybridization signal at 11 kb with cell line ER, but not with BIN40, which verifies the Dw4 specificity; cell line 256 was also positive. As shown in panel B, the Dw14 DNA probe reacted with cell-line BIN40 (Dw14 homozygous), but not ER (Dw4 homozygous); cell-line 256 was again positive, consistent with its heterozygous genotype.

Referring again to panel A, analysis of DNA from patients with rheumatoid arthritis showed that six of seven patients homozygous for DR4 carried a Dw4 DR$\beta$ gene; in addition, one of the DR4/5 heterozygous patients was positive for Dw4 (lane 9, panel A). Of the seven DR4 homozygous patients, six carried a Dw14 DR$\beta$ gene; five of these patients (lanes 4 to 7 and lane 10) were heterozygous for Dw4 and Dw14 genes. One of the patients heterozygous for DR4/5 (lane 11) carried Dw14 on the DR4 haplotype. Both DR4/5 individuals carried a 3.4 kb DR5 gene, as expected. One patient (lane 12) appeared to be Dw4 only, and one patient (lane 8) was Dw14 only. Thus, of the nine patients tested, seven were positive for Dw4 and seven were positive for Dw14.

Of the Caucasian control subjects, 55% of DR4+haplotypes were Dw4; 20% were Dw14. Of seven DR4 homozygous control individuals in a random blood donor panel, none were heterozygous for Dw4 and Dw14. Nepom, B. S., et al., J. Clin. Invest. 74:287–291, 1984. The unexpectedly high frequency of Dw14 among the DR4 rheumatoid arthritis patients examined here suggests that the Dw14 DR$\beta$ gene, in addition to the Dw4 gene, is linked with susceptibility to rheumatoid arthritis. The heterozygous combination of Dw4/Dw14 may increase the predisposition to develop rheumatoid arthritis.

While the preferred embodiments of the invention have been illustrated and described, it is to be understood that, within the scope of the appended claims, various changes can be made herein. Hence, the invention can be practiced in ways other than those specifically described herein.

The embodiments of the invention in which an exclusive property or privilege is claimed are defined as follows:

1. A probe useful for diagnosing predisposition to adult rheumatoid arthritis, comprising an oligonucleotide capable of specifically hybridizing with the nucleotide sequence $$5'\text{-TACGGGGTTGR}_1\text{GAGAGCTT-}3'$$

or $$3'\text{-AR}_2\text{GCCCCAACR}_3\text{CR}_2\text{CR}_2\text{CGAA-}5'$$

wherein A is adenine, C is cytosine, G is guanine, T is thymine, $R_1$ is GT or TG, $R_2$ is T or uracil, and $R_3$ is CA or AC.

2. The probe of claim 1, wherein said oligonucleotide comprises about 16 nucleotides.

3. A probe capable of hybridizing with the Dw14 DRβ1 allele, useful for diagnosing predisposition to adult rheumatoid arthritis, comprising at least 15 sequential nucleotides selected from the sequence

3'-TGCCCCAACR$_1$CTCTCGA-5' or

5'-ACGGGGR$_2$R$_2$GR$_3$GAGAGCR$_2$-3' wherein A is adenine, C is cytosine, G is guanine, T is thymine, $R_1$ is CA or AC, $R_2$ is T or uracil, and $R_3$ is GR$_2$ or R$_2$G.

4. The probe of claim 3, wherein the oligonucleotide comprises:

3'-CCCAACR$_1$CTCTCG-5' or

5'-GGGR$_2$R$_2$GR$_3$GAGAGC-3'.

5. The probe of claim 3, wherein the oligonucleotide is labeled with a detectable marker.

6. The probe of claim 5, wherein the detectable marker is selected from among enzymes, biotin, radionuclides, fluorophores, luminophores, enzyme inhibitors, coenzymes, luciferins, paramagnetic metals and spin labels.

7. A diagnostic kit useful for diagnosing predisposition to adult rheumatoid arthritis, comprising a first oligonucleotide probe capable of specifically hybridizing with the Dw4 DRβ allele in combination with a second oligonucleotide probe according to claim 1 capable of specifically hybridizing with the Dw14 DRβ allele.

8. The diagnostic kit of claim 7, wherein the Dw4 probe comprises at least 15 sequential nucleotides selected from the sequence

3'-TGCCCCAACCACTCTCGA-5' or

5'-ACGGGGRRGGRGAGAGCR-3' or

3'-CTCGTCTTGCCCGGCGC-5' or

5'-GAGCAGAAGCGGGCCGCG-3' wherein A is adenine, C is cytosine, G is guanine, T is thymine, and R is T or uracil.

9. The probe of claim 8, comprising

3'-CCCAACCACTCTCG-5' or

5'-GGGRRGGRGAGAGC-3' or

3'-CTCGTCTTCGCCCGG-5' or

5'-GAGCAGAAGCGGGCC-3'.

10. The diagnostic kit of claim 7, wherein the Dw14 probe comprises at least 15 sequential nucleotides selected from the sequence

3'-TGCCCCAACACCTCTCGA-5' or

5'-ACGGGGRRGRGGAGAGCR-3' or

3'-CTCGTCTCCGCCCGGCGC-5' or

5'-GAGCAGAGGCGGGCCGCG-3' wherein A is adenine, C is cytosine, G is guanine, T is thymine, and R is T or uracil.

11. The probe of claim 10, comprising

3'-CCCAACACCTCTCG-5' or

5'-GGGRRGRGGAGAGC-3' or

3'-CTCGTCTCCGCCCGG-5' or

5'-GAGCAGAGGCGGGCC-3'.

12. The diagnostic kit of claim 7, further comprising a substratum capable of binding nucleic acids or cells.

13. The diagnostic kit of claim 12, wherein the substratum comprises positively charged substituents.

14. The diagnostic kit of claim 7, further comprising a restriction endonuclease.

15. The diagnostic kit of claim 14, wherein the restriction endonuclease is EcoR I.

16. The diagnostic kit of claim 7, further comprising a detergent for permeabilizing cell membranes.

17. The diagnostic kit of claim 16, wherein the detergent comprises an octoxynol.

18. In a method of genetic screening for inherited disease comprising the steps of contacting patient nucleic acids with a probe comprising an oligonucleotide capable of specifically hybridizing with a disease-associated polynucleotide sequence, and detecting the presence or absence of the disease-associated sequence in the patient nucleic acids, the improvement comprising contacting the patient nucleic acids with restriction endonuclease EcoRI and with a probe capable of specifically hybridizing with the Dw4 DRβ allele, and associating hybridization of the probe on an EcoRI-digested 11 kb fragment with predisposition to adult rheumatoid arthritis.

19. In a method of genetic screening for inherited disease comprising the steps of contacting patient nucleic acids with a probe comprising an oligonucleotide capable of specifically hybridizing with a disease-associated polynucleotide sequence, and detecting the presence or absence of the disease-associated sequence in the patient nucleic acids, the improvement comprising contacting the patient nucleic acids with a probe according to claim 1 capable of specifically hybridizing with the Dw14 DRβ allele and associating hybridization of the probe with predisposition to adult rheumatoid arthritis.

20. In a method of genetic screening for inherited disease comprising the steps of contacting patient nucleic acids with a probe comprising an oligonucleotide capable of specifically hybridizing with a disease-associated polynucleotide sequence, and detecting the presence or absence of the disease-associated sequence in the patient nucleic acids, the improvement comprising contacting the patient nucleic acids with a first probe capable of specifically hybridizing with the Dw4 and DRβ allele and a second probe according to claim 1 capable of hybridizing with the Dw14 DRβ allele, and associating hybridization of either the first or second probe, or both, with predisposition to adult rheumatoid arthritis.

21. The method of claim 19, further comprising contacting the patient nucleic acids with restriction endonuclease EcoRI and associating hybridization of the probe on an EcoRI-digested 11 kb fragment with predisposition to adult rheumatoid arthritis.

22. The method of claim 20, further comprising contacting the patient nucleic acids with restriction endonuclease EcoRI and associating hybridization of at least one of the first and second probes with predisposition to adult rheumatoid arthritis.

* * * * *